(12) United States Patent
Israely

(10) Patent No.: US 11,357,608 B2
(45) Date of Patent: Jun. 14, 2022

(54) LEECH THERAPY DEVICE

(71) Applicant: Eyal Israely, Los Angeles, CA (US)

(72) Inventor: Eyal Israely, Los Angeles, CA (US)

(*) Notice: Subject to any disclaimer, the term of this patent is extended or adjusted under 35 U.S.C. 154(b) by 787 days.

(21) Appl. No.: 16/278,095

(22) Filed: Feb. 16, 2019

(65) Prior Publication Data
US 2020/0261198 A1 Aug. 20, 2020

(51) Int. Cl.
*A61D 3/00* (2006.01)
*A01K 1/06* (2006.01)
*A61M 1/00* (2006.01)
*A61K 35/62* (2006.01)
*A61M 39/02* (2006.01)

(52) U.S. Cl.
CPC .............. *A61D 3/00* (2013.01); *A01K 1/0613* (2013.01); *A61K 35/62* (2013.01); *A61M 1/984* (2021.05); *A61M 2039/0261* (2013.01)

(58) Field of Classification Search
CPC ...... B65D 43/16; B65D 23/003; B65D 25/32; B65D 25/005; A61D 3/00; A01K 1/0613; A01K 1/06; A61K 35/62; A61M 1/985; A61M 1/984; A61M 1/982; A61M 1/98
USPC ...... 220/810, 916, 751, 676; 604/6.15, 4.01, 604/403; 119/416, 652, 651; 138/92, 91
See application file for complete search history.

(56) References Cited

U.S. PATENT DOCUMENTS

| | | | | |
|---|---|---|---|---|
| 367,836 A * | 8/1887 | Nichols | ................ | B65D 25/04 220/557 |
| 559,697 A * | 5/1896 | Gallagher | ................ | B65D 1/04 215/6 |
| 2,129,983 A * | 9/1938 | Bacon | ................ | A61M 39/04 604/251 |
| 4,493,705 A * | 1/1985 | Gordon | ................ | A61J 1/10 128/DIG. 3 |
| 5,679,775 A * | 10/1997 | Boos | ................ | A61M 1/3679 530/351 |
| 8,403,899 B2 * | 3/2013 | Sherman | ............ | A61F 13/0203 604/304 |
| 9,522,230 B2 * | 12/2016 | Agarwal | ............ | A61M 1/0023 |
| 2005/0054968 A1 * | 3/2005 | Giannella | ........... | A61M 1/3627 604/6.15 |

(Continued)

FOREIGN PATENT DOCUMENTS

RU 2214288 C1 * 10/2003 ............ A61M 37/00

OTHER PUBLICATIONS

Translation of RU2214288, Andreev et al., Oct. 20, 2003, Fig. 1 (Year: 2003).*

*Primary Examiner* — Robert J Hicks

(57) ABSTRACT

A leech therapy device adapted to latch a medicinal leech to a predetermined wound site is provided. The leech therapy device includes a conduit extending between a first end to a second end; an inner diameter of the conduit dimensioned to receive a medicinal leech, the inner diameter being less than twice a girth of the medicinal leech; and a cutout provided in the conduit closer to the first end than the second end; the cutout extending over a surface area between 100 and 150 squared millimeters. Wherein a user places a medicinal leech into the inner diameter, wherein a head of the medicinal leech is adjacent to the cutout, and then the user selectively positions said leech therapy device so that the cutout substantially circumscribed the wound site so that the medicinal leech can engage the wound site.

16 Claims, 2 Drawing Sheets

(56) References Cited

U.S. PATENT DOCUMENTS

2014/0056850 A1\* 2/2014 Filutowicz ............. A01N 63/00
424/93.1

\* cited by examiner

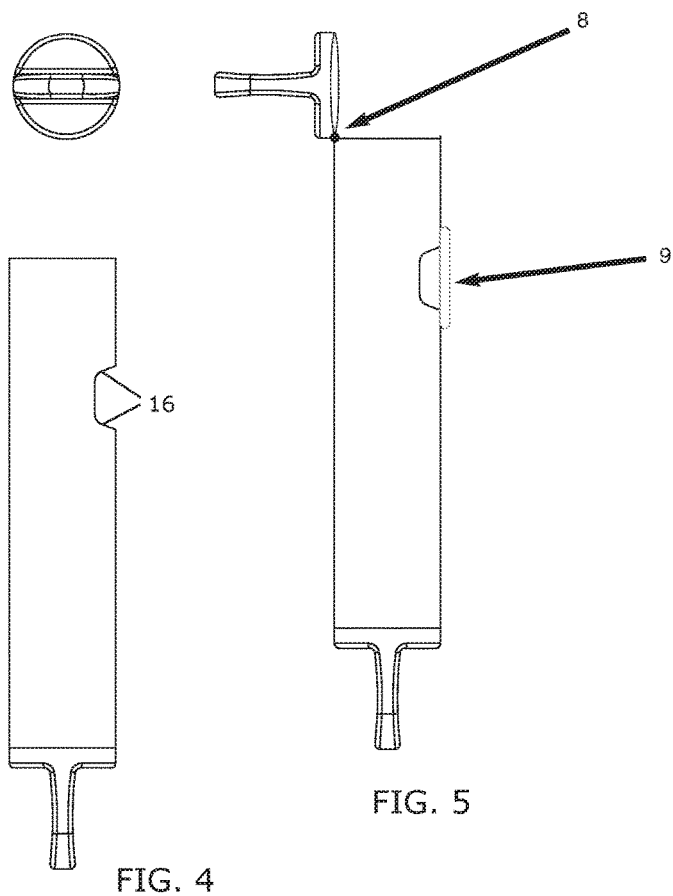
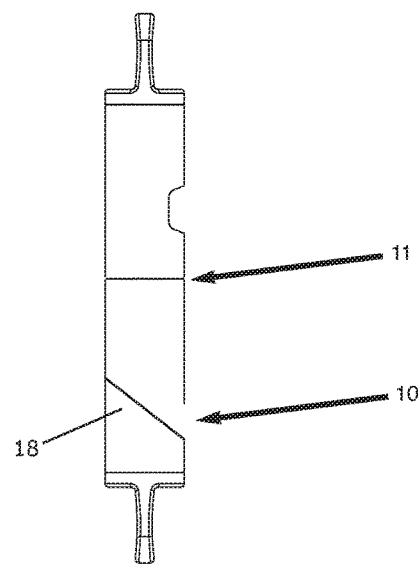
FIG. 4
FIG. 5
FIG. 6

LEECH THERAPY DEVICE

BACKGROUND OF THE INVENTION

The present invention relates to medical devices and, more particularly, to a leech therapy device adapted to latch a medicinal leech to a predetermined wound site.

Medicinal leeches are now making a comeback in microsurgery as they provide an effective means to reduce blood coagulation, to relieve venous pressure from pooling blood (venous insufficiency) and, in reconstructive surgery, to stimulate circulation in reattachment operations for organs with critical blood flow, such as fingers, eyelids, nose, lip, scalp and ears.

Since the 1960's, when British surgeons began applying leeches to post-operative regions of sutured tissue to encourage blood flow where venous blockage was present, the use of leech therapy has become more and more prevalent throughout the medical world.

Leeches are parasites that prey on warm blooded animals; however, only one species of leech is most commonly used in medicine. This creature has been well studied to provide doctors with reliable information on leech behavior, and can be raised in a sterile environment to a specified size for use in blood extraction.

Specifically, the leech has the following desired characteristics for the surface extraction of blood:

1) the leech can be placed near the wound site by a medical attendant;

2) the size of the leech head (about 1 cm in diameter) allows for close attachment at the edge of a closed wound;

3) the leech jaws can latch onto a shallow wound in the skins surface which produces no scarring;

4) the leech injects a histamine and an anticoagulant that aid in opening clogged capillaries;

5) the blood drained by the leech is drawn mainly from the venous capillaries, when finished, the leech detaches itself.

A leech's blood extraction generally occurs as follows: The leech attaches to the skin by a posterior sucker; and then the leech attaches its anterior sucker to the skin. (The anterior end is the leech's head that has the jaw, throat and secretion tissue.) A low-pressure region (vacuum) is formed in the leech throat by muscular expansion. The tissue around the jaw secretes a liquid form of an anesthetic, histamine and anticoagulant. The jaw sections are pressed against the skin surface and "rocked" to produce a sawing action. A wound is formed in the skin by the sawing action. The low pressure around the center of the jaw draws blood from the wound. After the throat cavity is filled, the leech ingests the crop. The pressure relief from the ingestion allows a back flow of the excreted fluid into the wound. (The vacuum is reduced over the wound during ingestion but is not entirely released.) The jaw is maintained in pressure against the skin with teeth extending into the wound without completely filling the opening. The jaw sawing action, fluid excretion, and throat vacuum are continued until the throat cavity fills again. The crop is repeatedly ingested until the leech is full. The leech detaches and is removed. (The leech takes less than one hour to fill itself.) The wound continues to bleed for several hours. Another leech can be placed on the extraction site.

Originally, medicinal leeches were administered by a medical attendant who placed the leech near the wound site, and then used mere physical persuasion to steer the leech's head with the hope that the leech would attach to the desired location. The disadvantages of such a "hands-on" administration include, among other things, consuming the time of hospital staff, which more likely than not have no formal training; unsettling the patient, who can observe the administration; and increasing the risk of "leech migration," where the leech moves away from the treatment area, possibly into body orifices or deeper into the wound itself.

Thereafter, several methods and devices were designed to more effectively attach the leech to the desired spot as well as prevent leech migration. For instance placing gauze with pre-cut holes around and in close contact with the area to be treated, leaving only the desired attachment site exposed—creating a sort of "leech corral." Though the so-called leech corral aims to form a barrier that lessens leech migration, the user still needs to steer the leech head to the hole in the gauze circumscribing the desired attachment site. Additionally, leeches can still traverse such "soft barriers."

Other methodologies teach the use of a surgical suture passed through the leech that is then tied to the dressing to prevent migration—though, in injuring the leech one would risk making the leech less effective—if not dead useless.

Applicators providing a rigid barrier in order to prevent migration have heretofore been jury-rigged contraptions missing components for securing the device to patients, but rather depend on continuous supervision by either the convalescent or an under-manned hospital staff throughout the therapeutic process; a process that includes up to 60 minutes for each leech's feeding, and that overall could last days. Furthermore, makeshift contraptions are not designed specifically for attaching leeches to the variety of flaps in need to leech therapy. Moreover, such contraptions tend to be made solely of plastic, and so generally offer poor surfaces for labeling or printing, and the labeling or printing that they do afford is often easily smudged.

As can be seen, there is a need for a leech therapy device adapted to latch a medicinal leech to a predetermined wound site.

SUMMARY OF THE INVENTION

In one aspect of the present invention, a leech therapy device includes a conduit extending between a first end to a second end; an inner diameter of the conduit dimensioned to receive a medicinal leech, the inner diameter being less than twice a girth of the medicinal leech; and a cutout provided in the conduit closer to the first end than the second end; the cutout extending over a surface area between 100 and 150 squared millimeters.

In another aspect of the present invention, the leech therapy device includes a conduit extending between a first end to a second end, wherein the conduit has a length between 100 and 300 millimeters; an inner diameter of the conduit of approximately two to three centimeters; a cutout provided in the conduit closer to the first end than the second end; the cutout extending over a surface area between 100 and 150 squared millimeters; an inward taper along both ends of the cutout; a removable closure pivotally attached to the first end; a rigid closure attached to the second end; a closure tab transversely extending from each closure; a tab hole provided in each closure tab; and an elastic band interconnected each tab hole.

In yet another aspect of the present invention, a method of applying leech therapy to a wound site includes the steps: providing the above-mentioned leech therapy device; placing a medicinal leech into the inner diameter, wherein a head of the medicinal leech is adjacent to the cutout; and selectively positioning said leech therapy device so that the cutout substantially circumscribed the wound site.

These and other features, aspects and advantages of the present invention will become better understood with reference to the following drawings, description and claims.

BRIEF DESCRIPTION OF THE DRAWINGS

FIG. 4 is a side elevation view of an exemplary embodiment of the present invention, shown with a removable closure 4 removed and shown from a top plan view;

FIG. 5 is an elevational view of an exemplary embodiment of the present invention; and FIG. 6 is a section view of an exemplary embodiment of the present invention, cut through along a longitudinal axis of the conduit so as to view an internal portion of the present invention.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Referring to FIGS. 1 through 6, the present invention may include a leech therapy device 20 adapted to facilitate the latching of a medicinal leech to a predetermined wound site, or in other words a "leech latcher." The device may provide a transparent or semitransparent conduit 1 of a flexible material which can be repeatedly bent and straightened out without fracture or losing its original cross-section profile throughout its length. The conduit 1 may have a uniform internal diameter defined by the girth of an engorged medicinal leech (not shown), or in other words may by range from one to three centimeters. The conduit 1 may have a thickness of approximately one to two mm and a length of roughly 100 to 300 mm. The conduit 1 is made by an injection molding, additive manufacture or like.

Figure 1:
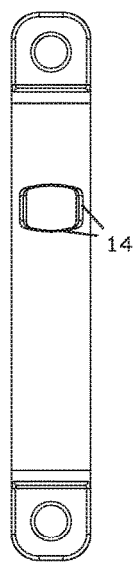
FIG. 1 is a front elevation view of an exemplary embodiment of the present invention.
Figure 2:
FIG. 2 is side elevation view of an exemplary embodiment of the present invention, rotated 90 degrees relative to FIG. 1.
Figure 3:
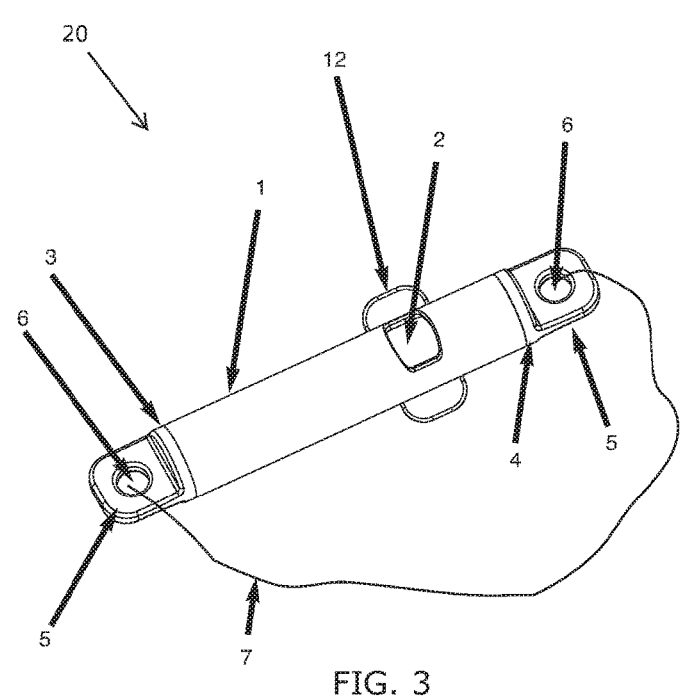
FIG. 3 is a perspective view of an exemplary embodiment of the present invention.

An off-center cutout 2 may be provided in the conduit at a predetermined distance from the edge of the conduit 1, as illustrated in FIG. 1. In the other embodiments, the cutout 2 may be centered. The cutout 2 may be formed in the same manufacturing process as the conduit 1, thereby saving time and eliminating complexity in the manufacturing process. The cutout 2 may be defined by a notch cutout from the cylindrical conduit 1 so as to expose cutout walls 14 have a length of approximately eleven to thirteen millimeters (mm). The cutout 2 provides the medicinal leech access to a wound site. The cutout 2 may be various shapes so long as the cutout 2 functions in accordance with the present invention as described herein; specifically, different shapes would accommodate different types of wound site locations, or flaps, while allowing the medicinal leech to use both types of suckers. For example, a rectangular shape may facilitate engaging a patient's scalp, while an oval shape which would facilitating engaging a patient's ear. The notch, as illustrated in FIG. 4, may provide an inward taper 16 of cutout walls 14 for facilitating engagement with the patient near the wound site. The off-center orientation of the cutout 2 enables the medicinal leech to grow in length while attached to and ingesting at the wound site. The inner diameter of the conduit may range from one to five centimeters. Some of the inner diameters forces the leech to elongate while engorging with blood as opposed to increase their girth.

At one end of the conduit 1 may be a fixed closure 3 which terminates in a tab 5. On the other end of the conduit 1 may be a removable closure 4 which terminates in a tab 5. In one embodiment, the removable closure 4 is connected to the conduit via a pivot point 8, such as a hinge, in order to prevent losing the removable closure 4 as it moves between an open and closed condition. The fixed closure 3 and the removable closure 4 may be formed in the same manufacturing process as the conduit 1 and cutout 2. Additionally, the removable closure 4 may be then punched out, separated from the conduit 1 and pivotally connected by to the conduit 1 at the pivot point 8.

The outer corners of the tab 5 are typically beveled or rounded to avoid snagging and personal injury, and act as gripping points. Each tab 5 may have a hole 6 for attaching an elastic band 7 that is used to secure the device 20 to a patient. Side handles 12 may be provided adjacent the cutout 2 for manipulating and securing the medical device.

Referring to FIG. 5, the leech therapy device 20 may provide a removable cover 9 for the cutout 2. Referring to FIG. 6, the leech therapy device 20 may provide a second cutout 10 with a ramp 18 formed into the conduit 1 on the opposite end of the conduit as the first cutout 2. A removable internal barrier 11 may be disposed therebetween.

A method of using the present invention may include the following. The leech therapy device 20 disclosed above may be provided. A user may load a medicinal leech through the end of the conduit 1 when the removable closure 4 is in the open condition, and then moving the removable closure 4 to the closed condition.

Next, the leech therapy device 20 is applied to a patient so that the cutout 2 circumscribes the predetermined wound site, and the cutout walls 14 act as an immediate rigid barrier thereto. The elongated nature of the conduit 1 prevents rotation of the leech therapy device 20 relative the wound site, while preventing the leech from migrating. The leech therapy device 20 is further secured by use of the elastic band 7 to secure the leech therapy device 20 in a desired position. Therefore, in hands-free use, the leech therapy device 20 prevents the medicinal leech from migrating or flopping off, and enables a user or caregiver to monitor the medicinal leech through the transparent walls of the conduit 1.

The present invention has advantages over vertically-applied devices, which tend to urge less effective leech attachment because leeches naturally attach to their host's skin using both their posterior sucker and feeding anterior suckers. Thus, in a vertical position, the leech either must attach using only its anterior sucker around the edge of the site intended for blood extraction or otherwise pile onto itself in an attempt to attach both suckers to the skin surrounding the intended site. As a result, the leech's posterior sucker may be forced onto the wound, impeding the desired unclogging of local circulatory passages. Moreover, the leech's inclination to attach to the skin using both suckers is constrained by the vertical barrier. Thus, vertical barriers urge a less secure attachment which in turn increases the likelihood of a premature detachment especially, if such device is withdrawn prior to leech satiation. The resulting force associated with removing the contraption would also contribute to the leech falling inconveniently when they are being removed, post feeding.

Furthermore, when the leech therapy device 20 is in use, secured by use of the elastic band 7 or held by some other method, the stiffness of the conduit 1 will allow relatively small bending yet maintain its internal diameter, preventing the conduit 1 from local buckling and injuring the medicinal leech therein.

To remove the leech therapy device 20, once the leech is satiated, one works in reverse of application: first one unattaches the elastic band 7, disengages the cutout walls 14 from the wound site, opens the removable closure 4 and slides the satiated leech out of the conduit 1. The presence of the leech therapy device 20 during disposure of the leech prevents unsightliness and problems of the satiated leech flopping onto the ground, and so facilitates efficient, orderly leech therapy.

The leech therapy device 20 offers a hands-free way of applying leech therapy that is simple enough to be taught to patients, greatly reducing the demand on, over-worked hospital professionals.

It should be understood, of course, that the foregoing relates to exemplary embodiments of the invention and that modifications may be made without departing from the spirit and scope of the invention as set forth in the following claims.

What is claimed is:

1. A leech therapy device, comprising:
   a conduit extending between a first end to a second end;
   an inner diameter of the conduit dimensioned to receive a medicinal leech, the inner diameter being less than twice a girth of the medicinal leech; and
   a cutout provided in the conduit closer to the first end than the second end; the cutout extending over a surface area between 100 and 150 squared millimeters.

2. The leech therapy device of claim 1, further comprising a removable closure pivotally attached to the first end.

3. The leech therapy device of claim 1, further comprising an inward taper along both ends of the cutout.

4. The leech therapy device of claim 2, further comprising a rigid closure attached to the second end.

5. The leech therapy device of claim 4, further comprising a closure tab transversely extending from each closure; and a tab hole provided in each closure tab.

6. The leech therapy device of claim 5, further comprising an elastic band interconnected each tab hole.

7. The leech therapy device of claim 1, further comprising one or more side handles adjacent to the cutout.

8. The leech therapy device of claim 1, further comprising a second cutout provided in the conduit closer to the second end than the first end; and a ramp extending from a periphery of the second cutout toward an inner portion of the conduit.

9. The leech therapy device of claim 1, further comprising a removable cover over the cutout.

10. The leech therapy device of claim 1, wherein the conduit has a length between 100 and 300 millimeters.

11. The leech therapy device of claim 1, wherein the inner diameter is approximately two to three centimeters.

12. A leech therapy device, comprising:
    a conduit extending between a first end to a second end, wherein the conduit has a length between 100 and 300 millimeters;
    an inner diameter of the conduit of approximately two to three centimeters;
    a cutout provided in the conduit closer to the first end than the second end; the cutout extending over a surface area between 100 and 150 squared millimeters;
    an inward taper along both ends of the cutout;
    a removable closure pivotally attached to the first end;
    a rigid closure attached to the second end;
    a closure tab transversely extending from each closure;
    a tab hole provided in each closure tab; and
    an elastic band interconnected each tab hole.

13. The leech therapy device of claim 12, further comprising one or more side handles adjacent to the cutout.

14. The leech therapy device of claim 12, further comprising a second cutout provided in the conduit closer to the second end than the first end; and a ramp extending from a periphery of the second cutout toward an inner portion of the conduit.

15. The leech therapy device of claim 12, further comprising a removable cover over the cutout.

16. A method of applying leech therapy to a wound site, comprising:
    providing the leech therapy device of claim 1;
    placing a medicinal leech into the inner diameter, wherein a head of the medicinal leech is adjacent to the cutout; and
    selectively positioning said leech therapy device so that the cutout substantially circumscribed the wound site.

* * * * *